United States Patent [19]

Riley

[11] Patent Number: 4,748,003
[45] Date of Patent: May 31, 1988

[54] CONTAINER FOR FLASH STERILIZATION

[75] Inventor: Edward D. Riley, Ipswich, Mass.

[73] Assignee: Riley Medical Incorporated, Newburyport, Mass.

[21] Appl. No.: 899,811

[22] Filed: Aug. 25, 1986

Related U.S. Application Data

[63] Continuation-in-part of Ser. No. 838,638, Mar. 11, 1986, abandoned.

[51] Int. Cl.[4] .................. A61L 2/24; G05D 16/00
[52] U.S. Cl. .................. 422/112; 422/9; 422/11; 422/20; 422/38; 422/39; 422/295; 422/296; 422/103; 220/203; 220/204; 220/371; 220/372; 137/536; 137/493.7
[58] Field of Search .................. 422/9, 11, 26, 38, 39, 422/295, 296, 103, 112, 113; 137/536, 439, 493.7; 220/204, 203, 371, 372; 134/94, 110

[56] References Cited

U.S. PATENT DOCUMENTS

| | | | |
|---|---|---|---|
| 1,687,641 | 10/1928 | Aalborg | 137/493 |
| 2,754,062 | 7/1956 | Von Wangenheim | 137/493 |
| 3,409,037 | 11/1968 | Nelson | 137/536 |
| 3,974,936 | 8/1976 | Gerdes | 220/204 |
| 4,105,407 | 8/1978 | Sanderson | 220/257 |
| 4,157,072 | 6/1979 | West | 137/493 |
| 4,196,166 | 4/1980 | Sanderson et al. | 422/114 |
| 4,251,482 | 2/1981 | Sanderson et al. | 422/26 |
| 4,349,118 | 9/1982 | Sanderson et al. | 220/201 |
| 4,374,570 | 2/1983 | Sanderson et al. | 422/26 |
| 4,457,327 | 7/1984 | Pepper | 422/114 |
| 4,551,311 | 11/1985 | Lorenz | 422/26 |

FOREIGN PATENT DOCUMENTS

| | | | |
|---|---|---|---|
| 0426823 | 7/1911 | France . | |
| 0000077 | 2/1979 | PCT Int'l Appl. | 422/296 |
| 8102108 | 8/1981 | PCT Int'l Appl. | 422/26 |
| 1074275 | 7/1967 | United Kingdom . | |

Primary Examiner—Kenneth M. Schor
Assistant Examiner—Lori-Ann Cody
Attorney, Agent, or Firm—Cesari and McKenna

[57] ABSTRACT

A sterilization container is provided with relatively large top and bottom apertures to allow hot steam to rapidly pervade the interior of the container through the top while flushing cool air out the bottom. The apertures are provided with pressure actuated valves with large cross sections to minimize impedance to gas flow when the valves are open. The pressure-sensitive elements of the valves are set such that the valves close to seal the apertures when the external pressure is at atmospheric, and rapidly open fully when the pressure begins to rise in the autoclave as steam is admitted at the start of a sterilization cycle. When the external pressure is returned to atmospheric at the end of the cycle, the pressure-actuated valves close to provide a sealed container for removal from the autoclave.

7 Claims, 3 Drawing Sheets

CONTAINER FOR FLASH STERILIZATION

CROSS REFERENCE TO RELATED APPLICATION

This application is a continuation-in-part of copending U.S. application Ser. No. 838,638, filed Mar. 11, 1986 now abandoned and entitled Container for Flash Sterilization.

BACKGROUND OF THE INVENTION

This invention relates to a container for articles to be sterilized by exposure to steam. More particularly, it relates to a container used for so called "flash sterilization," in which articles to be sterilized are exposed to high temperature steam for a short interval.

The invention concerns the sterilization of surgical instruments and the like in an autoclave where they are exposed to steam at an elevated temperature. The time required for sterilization depends on the temperature and in order to reduce this time to a minimum, the instruments are exposed briefly to steam at a temperature higher than that normally used in autoclaves. This "flash sterilization" is accomplished by suddenly filling the autoclave with saturated steam at an elevated pressure, e.g. 30 psig.

Flash sterilization works well in situations where the instruments are to be used immediately following sterilization and in proximity to the autoclave. In that case, the instruments may be merely wrapped in a towel or disposed in an open basket in the autoclave so that they will be exposed to the hot steam immediately on introduction of the latter to the autoclave.

On the other hand, problems arise if the instruments are not to be used immediately or must be transported an appreciable distance to the place of use. In order to prevent contamination before use, they must be kept in a closed container. In the autoclave the use of such a container has retarded the application of the hot steam to the instruments and thus has defeated the objective of flash sterilization, i.e., to rapidly render harmless microbial forms of life. It has been proposed to include filters in one or more walls of the container so that the steam can enter through the filters. However, filters which have a sufficiently fine structure to prevent the entry of contaminants after removal of the container from the autoclave impede the inflow of steam to such an extent that flash sterilization is not reliably accomplished.

SUMMARY OF THE INVENTION

Accordingly, it is an object of the present invention to provide an improved container for the flash sterilization of articles disposed therein.

Another object of the invention is to provide a sterilization container that quickly exposes articles contained therein to high pressure steam when the latter is introduced into an autoclave.

Another object of the invention is to provide a sterilization container of the above type which protects the contents thereof from contamination after removal from the autoclave and which is easily opened for quick access to the contents when the latter are to be used.

A sterilization container incorporating the invention has relatively large top and bottom apertures that are closed by pressure-sensitive valves. The valves seal the apertures at normal, i.e., atmospheric, pressure. When steam is introduced into an autoclave in which the container is disposed, the increase in pressure causes the valves to open, providing for relatively unhindered flow through both the bottom and the top of the container. Specifically, relatively cool air in the container flows down and out through the bottom aperture and hot steam enters through the top to replace the exiting air. The hot steam thus rapidly pervades the interior of the container and thereby rapidly sterilizes the contents thereof. When the pressure in the autoclave is reduced at the end of the sterilization process, the valves close, thereby sealing the apertures.

The sterilization container includes a cover that is removably sealed to a base unit by a gasket-and-toggle clamp arrangement. Together with the valves this seal isolates the interior of the container and thus prevents contamination of the contents thereof. The clamps can be quickly released from removal of the cover and rapid access to the contents.

DETAILED DESCRIPTION OF AN ILLUSTRATIVE EMBODIMENT

Figure 1:
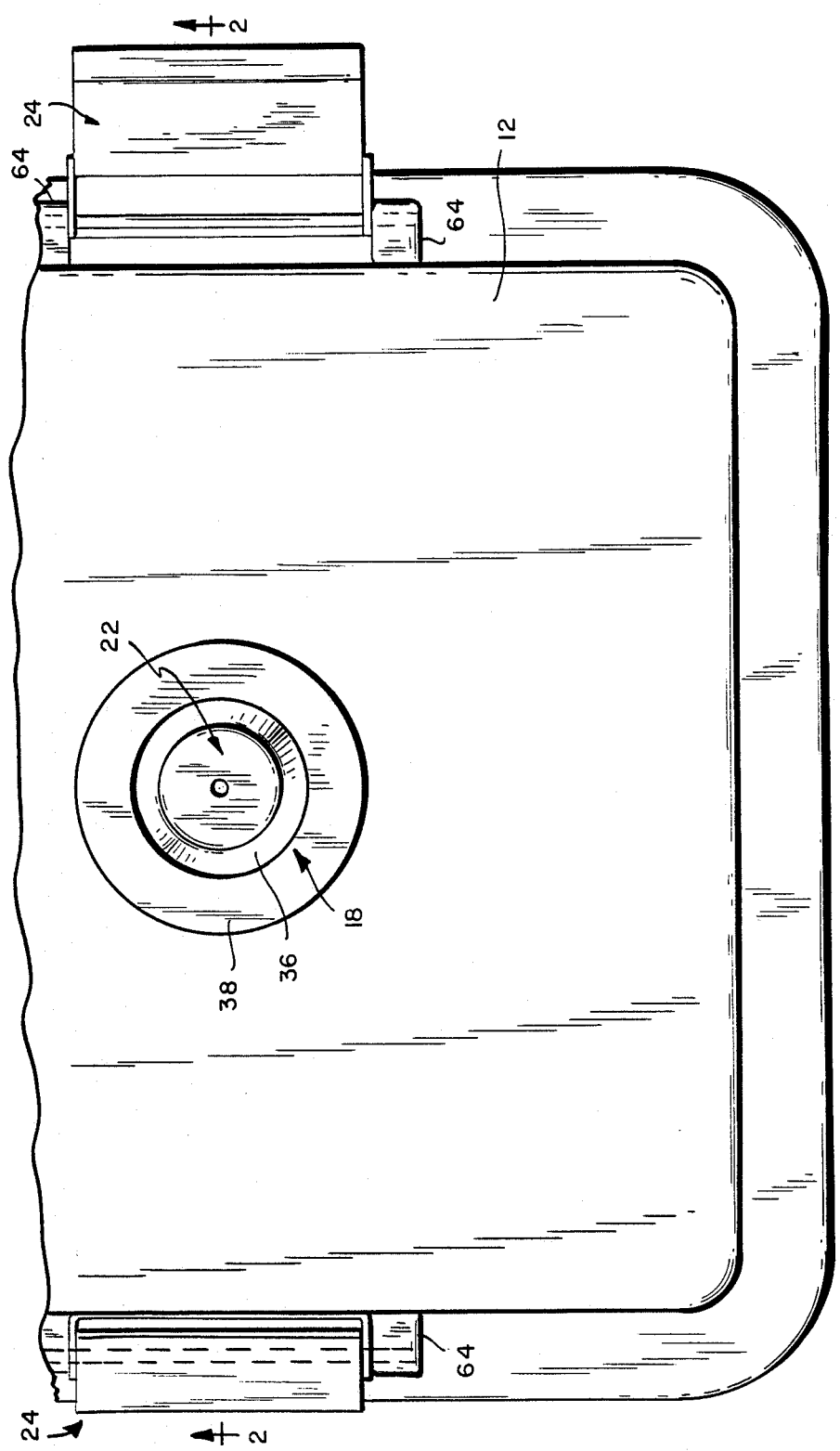
FIG. 1 is a fragmentary top view of a sterilization container incorporating the invention.

As shown in the drawing, a sterilization container embodying the invention comprises a base unit generally indicated at 10 and a cover unit, generally indicated at 12, removably sealed to the base unit. A perforated tray 14 supported on the base unit contains articles (not shown) to be sterilized in the container. The base unit is provided with an aperture 16 at its bottom and the cover unit 12 has an aperture 18 at the top of the container. The apertures 16 and 18 are sealed by pressure-actuated valves generally indicated at 20 and 22, respectively. The cover unit 12 is secured to the base unit 10 by means of a series of toggle clamps 24.

More specifically, the base unit 10 has sidewalls 26 that slope downwardly and inwardly toward the aperture 16 at the bottom. The upper ends of the sidewalls 26 terminate at a horizontal shelf 28 that supports the tray 14. The outer edge of the shelf 28 in turn terminates at a lip 30, having an inverted-U cross-section. The lip 30 is used in sealing the cover unit 12 to the base unit 10 as described below. The base unit 10 also includes a set of legs 32, integrally formed with the sidewalls 26, to support the container with the bottom aperture 16 and valve 20 spaced above the surface 34 on which the container rests.

Figure 2:
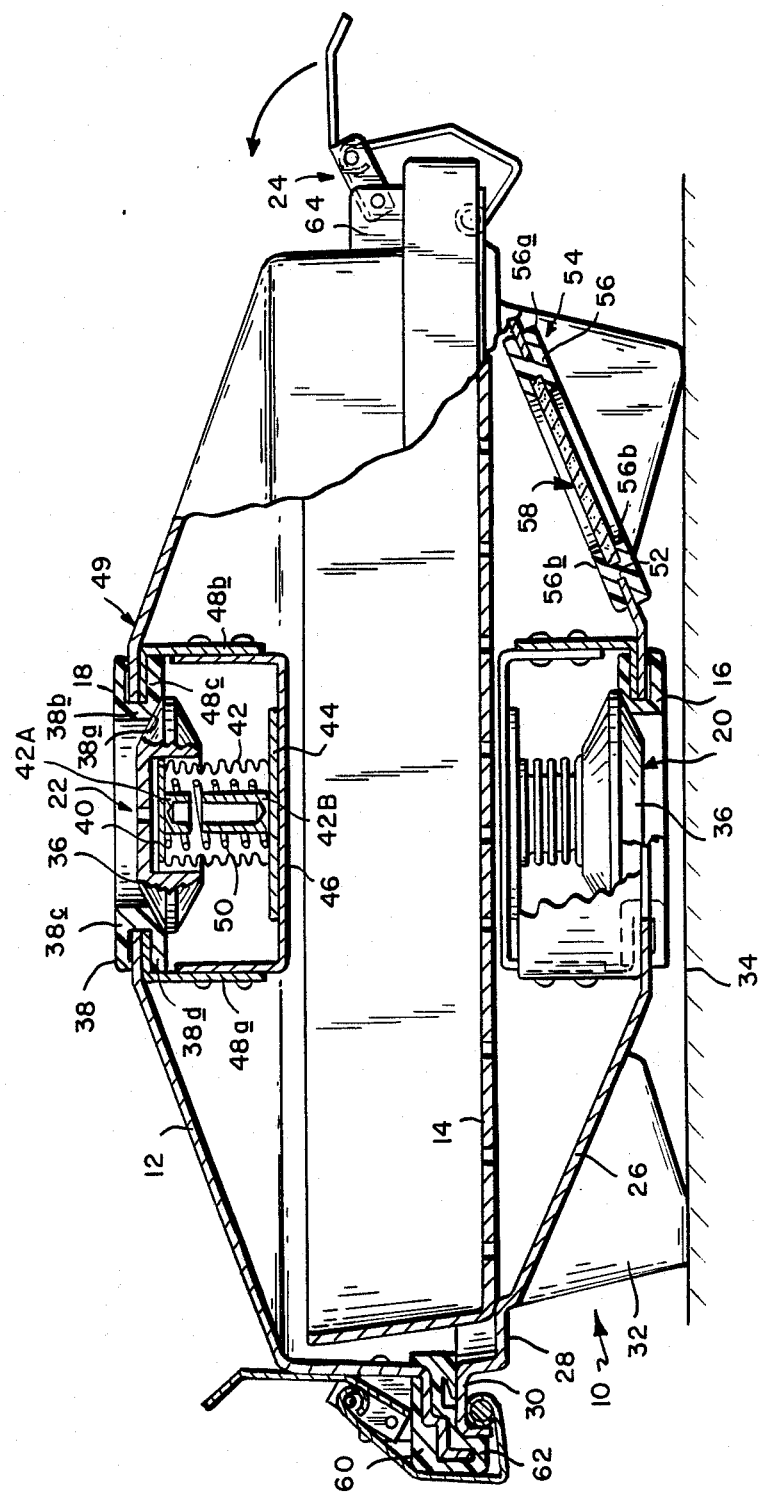
FIG. 2 is a view, partly in section, taken along line 2—2 of FIG. 1.

The valves 20 and 22 are preferably of identical construction. As shown in FIG. 2, the valve 22 comprises moveable valve member 36 which, in the closed position of the valve, bears against a seat surface 38A on a seating ring 38. Both the valve member 36 and the seating ring 38 are preferably of elastomeric material. The member 36 is fitted onto a plate 40 attached to the upper end of a bellows 42. The other end of the bellows is attached to a second plate 44 that seats against a U-Shaped bracket 46.

The bracket 46 in turn is fastened to a pair of arms 48A and 48B that extend downward from a ring 48C whose inner diameter is preferably the same as that of the aperture 18. The ring 48C and the bracket 46 supported thereby are maintained in place by the seating ring 38. Specifically, the ring 38 has a mid-portion 38B whose outer diameter corresponds with the diameter of the aperture 18. At opposite ends of the mid-portion 38B are annular extensions 38C and 38D above and below the top wall 49 of the cover unit 12. The ring 48C is sandwiched between the extension 38D and the cover unit 12. To assemble these parts to the cover unit, the ring 48C is held in position and the ring 38 is then "popped" into place.

The bellows 42 is preferably an evacuated metal bellows that is urged into its extended position by an internal compression spring 50. Thus, the spring 50 exerts a force causing moveable valve member 36 to bear against the seat surface 38A and to thereby close the valve. When the pressure external to the bellows increases above atmospheric pressure, e.g., by 2-3 psi, the resulting force on the bellows contracts the bellows against the force of the spring 50, thereby moving the valve member 36 away from the seat 38A. This opens the valve and provides communication between the interior and the exterior of the container through the aperture 18.

The ends of the bellows 42 are fitted with internal studs 42A and 42B. The studs provide a compression limit for the bellows 42, thereby protecting the bellows from over pressure.

The base unit 10 also includes an aperture 52 fitted with a filter assembly 54. The filter assembly 54 comprises an elastomeric ring 56 formed with outer annular extensions 56A and inner annular extensions 56B. The outer extensions 56A serve to fasten the filter assembly in place in the aperture 52. The inner extensions 56B secure a filter disk 58. The purpose of the filter assembly 54 is to equalize the internal pressure in the container 12 with the external atmospheric pressure. The filter disk 58 has a sufficiently fine structure to prevent contaminants from entering the container through the filter assembly.

A seal between the cover unit 12 and the base unit 10 is accomplished by means of a circular gasket 60 fitted to a lip 62 at the periphery of the cover unit 12. The gasket 60 seats against the lip 30 of the base unit 10 and it is held in place by the clamps 24. The clamps 24 can be simple over-center toggle clamps hinged to ears 64 that extend from and are integral with the cover unit 12.

In use, the container, with the clamps 24 in the secure position as shown on the left in FIG. 2, is inserted into an autoclave. For flash sterilization, steam is suddenly introduced into the autoclave and the pressure rises rather rapidly. As soon as the pressure reaches a few pounds above atmospheric pressure, it is sufficient to open the valves 20 and 22. The valve-opening force may be augmented somewhat by a pressure differential between the exterior and interior of the container, since the filter disk 58 can provide a sufficient restriction to air flow there through to retard the equalization of the internal and external pressures. With the valves open, the relatively cool air within the container flows downwardly and out through the valve 20, while steam from within the autoclave flows into the container through the valve 22. The rapid turnover of atmosphere within the container is aided by the slopes of the sidewalls 26 which guide air from the outer portions of the container downwardly and inwardly toward the valve 20.

The relatively large diameters of the moveable valve members 36 and the seat surfaces 38A provide a large cross-section for air flow through the valves when they are open. The valves thus offer negligible impedance to the flow required to bring high temperature steam rapidly into the interior of the container. The attainment of a large flow cross-section through the valves is assisted by evacuation of the bellows 42 so that the reaction force against the valve-opening pressure is a linear force provided by the spring 50. If, instead, gas pressure within the bellows were used to provide the bellows restoring force, the "spring constant" of the bellows would increase with bellows compression and the valve would therefore not open as much for a given pressure differential across it, given the same initial pressure required to unseat the valve member 36 from the seating surface 38A. Evacuation of the bellows 42 also largely eliminates temperature sensitivity of the restoring (closing) force of the valves.

Figure 3:
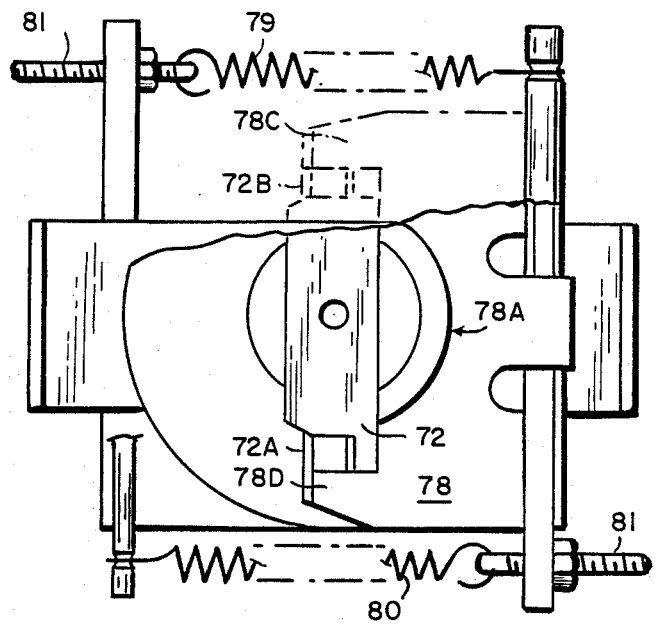
FIG. 3 is a fragmentary top view of a second valve arrangement used in the invention.
Figure 4:
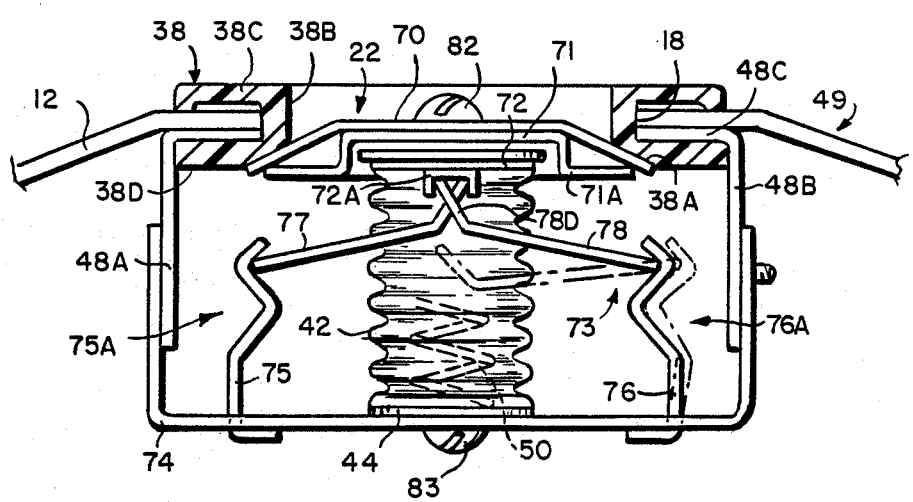
FIG. 4 is a side view, partly in section, of the section valve arrangement.

Another embodiment of the invention uses a valve arrangement illustrated in FIGS. 3 and 4. As shown in FIGS. 3 and 4, the valve 22 comprises a moveable valve member 70 which, in the closed position of the valve, bears against a seat surface 38A on seating ring 38. The valve member 70 is a shallow truncated hollow one with an open bottom and a solid top. The member 70 is fitted over a support member 71 which is a hollow cylinder approximately the height of the valve member 70 with a solid top and an open bottom. Around the bottom rim of support member 71 is an annular lip 71A the outer edge of which contacts the underside of the valve member 70 near its lower rim. The valve member 70 and the support member 71 are attached to a metal strip 72 which is in turn attached to the upper end of a bellows 42. Except as described below the bellows 42 in FIG. 4 is generally similar to the bellows 42 illustrated in FIG. 2. Both ends of the metal strip 72 are molded into inverted U-shaped gutters 72A and 72B for coupling with a spring-lever assembly 73. The other end of the bellows 42 is attached to a plate 44 that seats against a U-shaped mounting brackert 74.

The mounting bracket 74 is fastened to a pair of arms 48A and 48B that extend downward from a ring 48C whose inner diameter is preferably the same as that of the aperature 18. The ring 48C and the mounting bracket 74 supported thereby are maintained in place by the seating ring 38 in the same manner as the ring 48C of FIG. 2.

The spring-lever assembly 73 comprises two opposing hinge plates 75 and 76, two lever plates 77 and 78 and two tension springs 79 and 80. The hinge plates 75 and 76 are hinged to the bottom of the mounting bracket 74. The sides of the hinge plates are formed into S-shaped bends 75A and 76A, thus creating troughs into which the lever plates 77 and 78 fit. The lever plates 77 and 78 each have U-shaped cutouts 77A and 78A (only one of which is shown in FIG.3). The cutout 78A in lever plate 78 creates two arms 78C and 78D on opposite sides of the bellows 42. The arms 78C and 78D are bent upwards at the ends and are positioned in the U-shaped gutters 72A and 72B of the metal strip 72, thereby linking hinge plate 76 to the valve 22. Likewise, lever plate 77 is similar in shape to lever plate 78 and is disposed between hinge plate 75 and the U-shaped gutters 72A and 72B.

The springs 79 and 80 urge the hinge plates 75 and 76 toward each other. Moreover, each spring 79 and 80 is connected to the hinge plates by a bolt 81 which permits the spring tension between the hinge plates to be adjusted. The spring-lever assembly 73 thereby transmits the adjustable spring force of the two springs 79 and 80 upward to the valve member 70 and thus urges the valve member toward the closed position. By virtue of the geometry of the described linkage, it also creates an effective spring coefficient of the upward force vector which is negative over most of the distance of travel from the fully closed position of the valve to the fully open position.

The bellows 42 is positioned at the center of the spring-lever assembly 73 and is fastened to the valve member 70 by a screw 82 and to the mounting bracket by another screw 83. The bellows 42 is preferably an evacuated metal bellows that is urged into its extended position by an internal compression spring 50. The spring 50, in cooperation with the spring-lever assembly 73, exerts a force urging the moveable valve member 70 to the closed position against the seat 38A. Because of the assistance given by the spring-lever assembly 73, spring 50 in FIG. 4 need not have as large a spring constant as the spring 50 illustrated in FIG. 2.

When the pressure external to the bellows 42 increases above atmospheric pressure, e.g. by 5-10 psi, the contraction force on the bellows becomes greater than the sum of the internal spring force and the upward spring force of the spring-lever assembly 73 thereby moving the valve member 70 away from the seat 38A. This opens the valve and provides communication between the interior and the exterior of the container through aperture 18.

The spring-lever assembly 73 reduces the pressure range over which the valve member achieves complete opening as compared to a bellows actuated valve without the spring-lever assembly. Thus the valve assembly illustrated in FIGS. 3 and 4 opens sooner and more rapidly than the valve illustrated in FIG. 2, thereby exposing the surgical implements in the sterilizer container to the high temperature steam earlier in the autoclave sterilization cycle. Indeed, the characteristics of the tension springs 79 and 80 and the spring 50 may be selected so that the net upward force exerted on the valve member 70 is substantially constant over the opening range of the valve member 70. In that case, when the net upward force is overcome by the the pressure in the autoclave, the valve member 70 will suddenly travel to its full open position.

I claim:

1. A container for sterilization of articles contained therein shaped for insertion into a sterilization unit, said container comprising:
   A. A base unit forming a bottom of said container,
   B. A cover unit forming a top of said container,
   C. Means for releasably securing said cover unit to said base unit thereby forming said container,
   D. Means forming apertures at the top and bottom of said container, and
   E. Pressure actuated valves which close to seal said apertures when the pressure external to said container is at about atmospheric and which fully open to provide negligible impedance to gas flow through said apertures when said pressure is at or above a predetermined level above atmospheric said apertures located such that gas flows freely into, through, and out of said container via said valves.

2. The container defined in claim 1 including a filter providing communication between the exterior and interior of said container to equalize the interior pressure with the exterior pressure.

3. The container defined in claim 1 in which each of said valves comprises a valve member and pressure-sensitive actuating means for moving said valve member to open and close said valve, said actuating means comprising an evacuated bellows and spring that urges said bellows into an extended condition, whereby an increase in the pressure external to said bellows causes said bellows to compress against said spring and move said valve member into the open position of said valve.

4. The container defined in claim 1 in which each of said valves comprises a valve member; a spring-lever means for exerting a force with a negative effective spring coefficient against the valve member, thereby urging said valve to a closed position; and a pressure-sensitive actuating means for moving said valve member to open and close said valve.

5. The container defined in claim 4 wherein said actuating means is an evacuated bellows and a spring which urges said bellows to an extended position.

6. The container defined in claim 1 in which said predetermined level atmospheric is in the range of from about 2 to 10 psi.

7. The container defined in claim 6 in which said predetermined level above atmospheric is in the range of from about 5 to 10 psi.

* * * * *